United States Patent
Alqathami

(10) Patent No.: US 10,751,431 B2
(45) Date of Patent: Aug. 25, 2020

(54) POSITRON EMISSION CAPSULE FOR IMAGE-GUIDED PROTON THERAPY

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Mamdooh Alqathami, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 1099 days.

(21) Appl. No.: 15/191,105

(22) Filed: Jun. 23, 2016

(65) Prior Publication Data

US 2017/0368209 A1  Dec. 28, 2017

(51) Int. Cl.
   *A61B 5/05* (2006.01)
   *A61K 51/12* (2006.01)
   (Continued)

(52) U.S. Cl.
   CPC .......... *A61K 51/1262* (2013.01); *A61B 6/032* (2013.01); *A61B 6/037* (2013.01);
   (Continued)

(58) Field of Classification Search
   None
   See application file for complete search history.

(56) References Cited

U.S. PATENT DOCUMENTS

2005/0171425 A1*  8/2005  Burke ................ G01R 33/286
                                                    600/420
2005/0260355 A1*  11/2005  Weber ................ A61L 27/303
                                                    427/566
(Continued)

FOREIGN PATENT DOCUMENTS

CN         103315944 B    3/2016
JP         5079510 B2     11/2012
                (Continued)

OTHER PUBLICATIONS

Abboud, F., et al., "An Experimental Palladium-103 Seed (OptiSeed(exp)) in a Biocompatible Polymer without a Gold Marker: Characterization of Dosimetric Parameters including the Interseed Effect", URL: http://scitation.aip.org/content/aapm/journal/medphys/35/12/10.1118/1.3006151, Medical Physics, vol. 35, No. 12, 3 Pages total, (Dec. 2008) (Abstract only).

(Continued)

*Primary Examiner* — Joel F Brutus
(74) *Attorney, Agent, or Firm* — Oblon, McClelland, Maier & Neustadt, L.L.P.

(57) ABSTRACT

Multi-modal imaging capsule for image-guided proton beam therapy, consisting of a biocompatible polymer layer, $^{18}O$-enriched water, and a contrast agent. The biocompatible capsule may be inserted near or inside a tumor under the guidance of X-ray, magnetic resonance, or ultrasonography imaging. Upon proton beam irradiation, the capsule emits positrons, allowing the tumor to be imaged and tracked by a PET detector.

20 Claims, 20 Drawing Sheets

(51) Int. Cl.
*A61N 5/10* (2006.01)
*A61B 6/03* (2006.01)
*G01R 33/48* (2006.01)
*A61K 51/02* (2006.01)
*A61K 49/00* (2006.01)
*A61B 90/00* (2016.01)
*A61B 8/08* (2006.01)
*A61B 6/12* (2006.01)

(52) U.S. Cl.
CPC .......... *A61K 49/0002* (2013.01); *A61K 51/02* (2013.01); *A61N 5/1039* (2013.01); *A61N 5/1071* (2013.01); *G01R 33/481* (2013.01); *A61B 6/12* (2013.01); *A61B 8/0841* (2013.01); *A61B 2090/392* (2016.02); *A61B 2090/3954* (2016.02); *A61B 2090/3966* (2016.02); *A61B 2090/3995* (2016.02); *A61N 2005/1052* (2013.01); *A61N 2005/1054* (2013.01); *A61N 2005/1087* (2013.01)

(56) References Cited

U.S. PATENT DOCUMENTS

| | | | |
|---|---|---|---|
| 2009/0016960 A1* | 1/2009 | Selwyn | A61K 51/1251 424/9.1 |
| 2009/0035212 A1* | 2/2009 | Kihara | B01D 59/04 423/579 |
| 2010/0113861 A1* | 5/2010 | Biris | A61K 9/0009 514/1.1 |
| 2011/0104052 A1 | 5/2011 | Barnett et al. | |
| 2015/0087960 A1 | 3/2015 | Treffert | |

FOREIGN PATENT DOCUMENTS

| | | |
|---|---|---|
| JP | 5889337 B2 | 3/2016 |
| WO | 2009/114117 A2 | 9/2009 |

OTHER PUBLICATIONS

Cho, J., et al., "Feasibility of Proton-Activated Implantable Markers for Proton Range Verification using PET", Physics in Medicine & Biology, vol. 58, No. 21, pp. 7497-7512, (Nov. 7, 2013).

Dendooven, P., et al., "Short-Lived Positron Emitters in Beam-On PET Imaging during Proton Therapy", Physics in Medicine & Biology, vol. 60, pp. 8923-8947, (Nov. 5, 2015).

Kilbourn, M.R., et al., "A Simple 18O Water Target for 18F Production", The International Journal of Applied Radiation and Isotopes, vol. 35, No. 7, pp. 599-602 (Jul. 1984) (Abstract only).

Perez-Campana, C., et al., "Production of 18 F-Labeled Titanium Dioxide Nanoparticles by Proton Irradiation for Biodistribution and Biological Fate Studies in Rats", Particle & Particle Systems Characterization, vol. 31, pp. 134-142, (2014).

Perez-Campana, C., et al., "Tracing Nanoparticles In Vivo: a New General Synthesis of Positron Emitting Metal Oxide Nanoparticles by Proton Beam Activation", Analyst, vol. 137, pp. 4902-4906, (2012).

Cho, J., et al., "Feasibility of Hydrogel Fiducial Markers for In Vivo Proton Range Verification using PET", Physics in Medicine & Biology, vol. 61, 3 Pages total, (Feb. 23, 2016) (Abstract only).

Zhu, X., et al., "Proton Therapy Verification with PET Imaging", Theranostics, vol. 3, No. 10, pp. 731-740, (Sep. 19, 2013).

* cited by examiner

POSITRON EMISSION CAPSULE FOR IMAGE-GUIDED PROTON THERAPY

BACKGROUND OF THE INVENTION

Technical Field

The present invention relates to a multi-modal imaging capsule made of an encapsulating biocompatible polymer, $^{18}$O-enriched water, and a contrast agent, and methods of use for image-guided proton therapy.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancer continues to be the leading cause of mortality this century. A recent investigation by the International Agency for Research on Cancer (IARC) estimated that approximately 7.5 million deaths globally resulted from cancer, with approximately 13 million new cases being diagnosed per year. Radiotherapy is currently one of the most common and effective treatment modalities for delivering high curative or palliative ionizing radiation doses. It is estimated that more than one-half of all cancer patients receive radiotherapy during the course of their treatment. Significant developments to radiotherapy delivery techniques have been made within the last decade. For example, electron linear accelerators (LINAC) have been introduced, which generate higher energy photons and electron beams in the megavoltage energy range. These are currently considered the most common sources of clinical ionizing radiation. Modern photon radiotherapy techniques, particularly stereotactic radiosurgery (SRS) and intensity modulated radiotherapy (IMRT), were shown to produce conformal doses to tumors with high precision. In addition, accurate delivery of the radiation dose to tumors can also be enhanced through the use of imaging equipment such as that used in Image-guided radiotherapy (IGRT) to better localize the tumors. However, radiotherapy using photons suffers from a number of issues. For example, they have a high entrance dose and thus, deliver unnecessary radiation to skin and normal surrounding organs/tissues adjacent to the tumor. As a result, other radiotherapy treatment delivery modalities, such as proton therapy, have been gaining interest over the last few years with approximately 80,000 patients treated in 30 centers in the USA, Europe, and Asia.

Proton therapy is currently considered one of the most precise treatment delivery techniques of radiotherapy. Unlike a photon beam which has a high entrance dose and decreases gradually while passing through the body, a proton beam can penetrate through tissues and deposit most of its energy at the Bragg peak, which is located at the end of its track. In clinics, a spread-out Bragg peak (SOBP) field can be generated by using protons of multiple energies. Proton therapy was shown to provide better dose concentration at the tumor and has a proven role in the management of orbital tumors such as base of skull sarcomas as a result of the increased energy deposition toward the finite range of its beam in tissue. Compared to photon therapy, proton therapy has a much lower entrance dose and no dose beyond the target volume. Because of this unique depth-dose characteristic, proton therapy is able to deliver highly conformal radiation fields to target volumes with minimal side effects. Therefore, it is favored for tumors with irregular shapes or tumors in close proximity to critical organs. Proton therapy is recommended for the treatment of pediatric patients. However, proton therapy is sensitive to uncertainties in treatment planning and delivery compared to conventional photon radiotherapy. The most common concern is the accuracy of range of the proton. Because of the steep dose gradient and dose fall-off at the SOBP region, uncertainties in proton therapy planning or delivery have greater consequences than conventional photon therapy. For example, an error in estimating the accurate proton beam range could lead to a portion of the tumor not receiving the prescribed radiation dose, or normal organs situated away from the beam receiving more than the tolerance radiation dose. Since the proton therapy beam ends completely in the body, direct in vivo verification treatment monitoring is difficult. In order to ensure the effectiveness of proton therapy, there is a need for a device/system that would help evaluate the real-time location of the tumor during treatment.

It is known that irradiation with a proton beam leads to tissue-activation [Dendooven P et al., 2015 Short-lived positron emitters in beam-on PET imaging during proton therapy Phys. Med. Biol. 60 8923—incorporated herein by reference in its entirety]. This means that positron emission tomography (PET) can be used as a proton range verification tool because of its ability to image tissue activation. However, human tissues are made primarily from carbon, oxygen, hydrogen and nitrogen. Proton activation of these elements produces radionuclides of very short half-lives ranging from a few seconds to minutes. This requires an installation of an expensive in-beam PET scanner. This also makes it extremely difficult to use on-site or off-site PET scanners because of the short half-life of the radionuclide produced. Also, activation of tissues produces low activation probabilities that last for only a few seconds or minutes. Certain materials, in particular 18-oxygen ($^{18}$O)-enriched water, can be converted to 18-Fluorine ($^{18}$F) radioisotope by irradiation with a proton beam [Kilbourn M R et al., 1984 A simple 18O water target for 18F production Int. J. Appl. Radiat. Is. 35 599-602—incorporated herein by reference in its entirety]. The idea of using $^{18}$O-enriched water as a proton-activatable marker has also been explored [Jongmin C et al., 2013 Feasibility of proton-activated implantable markers for proton range verification using PET Phys. Med. Biol. 58 7497—incorporated herein by reference in its entirety]. However, the lack of a robust delivery device remains a major shortcoming for clinical application. For example, because the activated radioisotopes are not confined, PET signal distribution washout is a major issue for using this technique in a clinical setting. In addition, even if the $^{18}$O-enriched water is mixed with water-based (e.g., hydrogel) material [Jongmin C et al., 2016 Feasibility of hydrogel fiducial markers for in vivo proton range verification using PET Phys. Med. Biol. 61 2162—incorporated herein by reference in its entirety], the $^{18}$O-enriched water would easily diffuse into the surrounding tissues and organs. This not only increases the chances of PET signal washout but also increases the risk of an uncontrolled distribution of radioisotopes (i.e., $^{18}$F) after proton beam activation which poses a risk to patients. Therefore, in order for the PET signal measurement to verify proton therapy, any implanted positron emitter must be in a static, rather than diffusing, state to limit signal washout and an uncontrolled diffusion of radioisotopes.

Accordingly, there is a need for a robust proton-activated device for in vivo verification of the range of clinical proton therapy treatment and also for the evaluation of target motion during and between proton therapy treatments. This also includes visibility on common imaging modalities utilized in radiotherapy, in particular, computed tomography (CT) and magnetic resonance imaging (MRI).

In view of the foregoing, one objective of the present disclosure is to provide an implantable radiation-absorbing (radiopaque) capsule for proton therapy range verification and image registration during proton therapy treatment.

BRIEF SUMMARY OF THE INVENTION

According to a first aspect, the present disclosure relates to a positron emitter capsule which includes a biocompatible encapsulating polymer layer, a volume of $^{18}$O-enriched water encapsulated by the polymer layer, and a contrast agent which is active under magnetic resonance imaging (MRI) or X-ray imaging.

In one embodiment, the capsule has a shortest dimension of 0.8 to 2 mm and a longest dimension of 2 to 20 mm.

In another embodiment, the contrast agent is a metallic particle with a largest dimension less than 1 μm.

In one embodiment, the contrast agent is at least one metallic particle or metallic compound selected from the group consisting of barium, bismuth, cobalt, copper, gadolinium, gold, hafnium, iridium, iron, manganese, nickel, palladium, platinum, rhenium, silver, tantalum, thallium, titanium, tin, tungsten, and vanadium.

In one embodiment the contrast agent is a metal oxide.

In another embodiment this metal oxide is barium oxide, bismuth oxide, cobalt oxide, copper oxide, gadolinium oxide, hafnium oxide, iridium oxide, iron oxide, manganese oxide, nickel oxide, palladium oxide, silver oxide, tantalum oxide, thallium oxide, titanium oxide, tin oxide, tungsten oxide, or vanadium oxide.

In one embodiment the contrast agent is located on an external surface of the polymer layer, dispersed within the polymer layer, dispersed within the volume of $^{18}$O-enriched water, or any combination thereof.

In one embodiment the contrast agent is present in the form of agglomerates having a largest dimension between 50 nm and 2 μm, and the agglomerates are dispersed on an external surface of the polymer layer or dispersed within the polymer layer.

In another embodiment the external surface of the biocompatible polymer layer is corrugated or knurled to limit movement within an organism.

In one embodiment the polymer layer is a polymer such as a fluoropolymer, a polyarylether ketone, a polyether, a polyester, a polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, or a polysiloxane.

In one embodiment the capsule includes a second stable isotope, present as part of a molecule or compound, and the second stable isotope is capable of being proton-activated into a positron-emitting isotope.

In another embodiment the stable isotope is $^{89}$Y, $^{63}$Cu, $^{65}$Cu, $^{64}$Zn, $^{66}$Zn, $^{67}$Zn, $^{68}$Zn, $^{70}$Zn, $^{69}$Ga, $^{71}$Ga, $^{30}$Si, $^{15}$N, $^{13}$C, or $^{11}$B.

According to a second aspect, the present disclosure relates to a method of treating a tumor in an organism with a proton beam, by administering the capsule to the organism, locating the capsule with computed tomography (CT), magnetic resonance imaging (MRI), ultrasonography, or X-ray imaging, from a signal produced by the capsule, irradiating the tumor and capsule with a proton beam from outside the organism to convert $^{18}$O-enriched water to an aqueous radioisotope $^{18}$F$^-$ fluoride ion within the capsule by a photonuclear reaction with the proton beam, whereby the radioisotope $^{18}$F$^-$ fluoride ion emits positrons, and imaging the tumor and tumor environment by measuring the emitted positrons with a positron emission tomography (PET) detector to produce a first set of image and location data.

In one embodiment, the capsule is administered by injecting the capsule into the organism, next to or inside the tumor.

In another embodiment, the capsule is administered orally.

In one embodiment the positron emission tomography detector is located off-site in relation to the proton beam.

In one embodiment the proton beam irradiation of the capsule and tumor is repeated to produce a second set of emitted positrons.

In one embodiment, this second set of emitted positrons is imaged to produce a second set of image and location data.

In one embodiment, this second set of image and location data is compared to the first set in order to track the movement of the tumor.

In another embodiment, this second set of image and location data is compared to the first set in order to track the movement of the capsule.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
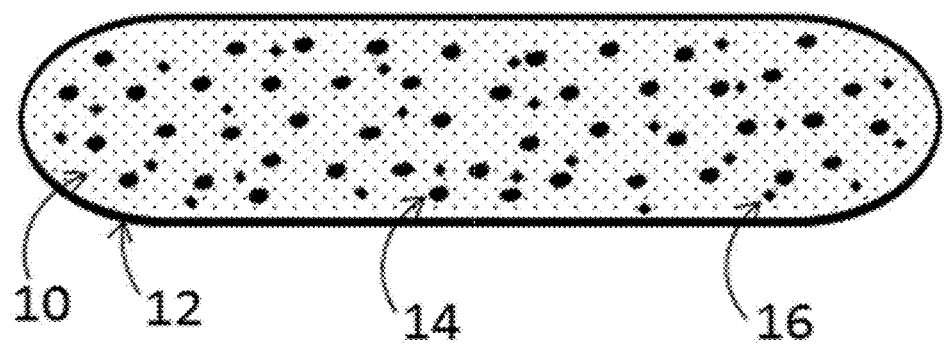
FIG. 1 is an embodiment of a positron emitter capsule containing two types of contrast agents.

Embodiments of the present disclosure will now be described more fully hereinafter with reference to the accompanying drawings, in which some, but not all embodiments of the disclosure are shown.

The present disclosure will be better understood with reference to the following terms and meanings set forth below. Unless defined otherwise, all technical and scientific terms used herein have the same meaning as commonly understood to one of ordinary skill in the art.

As used herein, the term "capsule" denotes an object that encloses an interior volume of liquid and/or gas.

As used herein, the term "biocompatible" denotes being biologically compatible by not producing a toxic, injurious, or immunological response when in physical contact with a living cell or tissue.

As used herein, the term "computed tomography" or "CT" refers to a type of imaging that uses X-rays, and thus, a contrast agent active under X-ray imaging would be active under CT imaging.

As used herein, the term "polymer" refers to macromolecular materials prepared from one monomer such as a homopolymer or to materials prepared from two or more monomers such as a copolymer, terpolymer, or the like.

As used herein, the term "polymer layer" refers to an impermeable coating including one or more polymers. This coating may be thick enough to be embedded with microparticles or other compounds.

As used herein, the term "contrast agent" is any composition of matter added to a subject to increase or decrease the signal strength of a particular mode of medical imaging for improved visibility of a feature. The signal either comes from the contrast agent itself, from its immediate environment, or both.

As defined herein, a contrast agent active under X-ray imaging is a compound that increases the radiodensity of the capsule, to at least 100, preferably to at least 200, more preferably to at least 300, even more preferably to at least 500 Hounsfield Units (HU).

A contrast agent active under MRI imaging is a compound that increases the spin-lattice relaxation rate ($r_1$) or the spin-spin relaxation rate ($r_2$) of nearby molecules. This concentration-dependent activity is measured in terms of concentration and time, and is also dependent on magnetic field strength, temperature, and solution environment [Rohrer M et al., 2005 Comparison of Magnetic Properties of MRI Contrast Media Solutions at Different Magnetic Field Strengths *Invest Radiol* 40 715—incorporated herein by reference in its entirety]. As defined here, a contrast agent being active under MRI imaging means that in human plasma at 37° C. and under a magnetic field strength of 1.5 T, the contrast agent has a an $r_1$ or $r_2$ of at least 3 mM$^{-1}$s$^{-1}$, more preferably at least 4 mM$^{-1}$s$^{-1}$.

As used herein, the term "polymeric matrix" refers to a porous meshwork of one or more polymers.

As used herein, the term "proton beam therapy" refers to irradiating tissue on or within an organism with a beam of protons. The term is used synonymously with "proton therapy" and "proton radiation therapy."

As used herein, the term "tumor" refers to all neoplastic cell growth and proliferation, whether malignant or benign, and all pre-cancerous and cancerous cells and tissues.

The term "cancer" refers to or describes the physiological condition in mammals that is typically characterized by unregulated cell growth.

According to a first aspect, the present disclosure relates to a positron emitter capsule which includes a biocompatible encapsulating polymer layer, a volume of $^{18}$O-enriched water (H$_2$$^{18}$O), wherein the $^{18}$O-enriched water is encapsulated by the polymer layer, and a contrast agent which is active under magnetic resonance imaging (MRI) or X-ray imaging.

As used herein, H (hydrogen) includes both $^1$H and the isotope deuterium (D or $^2$H). For example, H$_2$$^{18}$O includes $^1$H$_2$$^{18}$O, $^1$HD$^{18}$O, and/or D$_2$$^{18}$O.

In nature, oxygen exists in 3 stable isotopes: $^{16}$O, $^{17}$O, and $^{18}$O. Of these, $^{16}$O is the most abundant (>99 mol %), followed by $^{18}$O (0.2 mol %), and $^{17}$O (0.02 mol %). These isotopes of oxygen can be present in water as H$_2$$^{16}$O, H$_2$$^{17}$O, and H$_2$$^{18}$O. As used herein, "$^{18}$O-enriched water" refers to water containing at least 1 mole percent, preferably at least 50 mole percent, more preferably at least 95 mole percent, even more preferably at least 97 mole percent H$_2$$^{18}$O, with the remaining composition of water containing H$_2$$^{16}$O and/or H$_2$$^{17}$O. Commercial preparations of $^{18}$O-enriched water are available with purities of 97% H$_2$$^{18}$O or greater. The weight of the $^{18}$O-enriched water in a capsule may make up 1-95%, preferably 5-90%, more preferably 10-85% of the total capsule weight.

It is further envisioned that other sources of $^{18}$O could be used in place of, or in addition to, H$_2$$^{18}$O. These sources may have one or more $^{18}$O atoms within their structure, and combinations of these sources may be used within a single capsule. When used in place of H$_2$$^{18}$O, these sources may exist in an aqueous or an anhydrous environment within the capsule. These $^{18}$O sources include, but are not limited to, acetaldehyde-$^{18}$O, acetic acid-$^{18}$O, adipic acid-$^{18}$O, ammonium nitrate-$^{18}$O, barium carbonate-$^{18}$O, benzoic acid-$^{18}$O, benzophenone-$^{18}$O, calcium carbonate-$^{18}$O, carbon dioxide-$^{18}$O, carbon monoxide-$^{18}$O, carbonyl sulfide-$^{18}$O, cyclopentanone-$^{18}$O, dimethylformamide-$^{18}$O, ethanol-$^{18}$O, glycine-$^{18}$O, glucose-$^{18}$O, glycerol-$^{18}$O, hydrogen peroxide-$^{18}$O, leucine-$^{18}$O, maltose-$^{18}$O manganese carbonate-$^{18}$O, methanol-$^{18}$O, nitric acid-$^{18}$O, nitric oxide-$^{18}$O, nitrous oxide-$^{18}$O, nitrogen dioxide-$^{18}$O, oxygen gas-$^{18}$O, paraformaldehyde-$^{18}$O, phenol-$^{18}$O, phosgene-$^{18}$O, potassium carbonate-$^{18}$O, potassium nitrate-$^{18}$O, potassium nitrite-$^{18}$O, silicon dioxide-$^{18}$O, sodium acetate-$^{18}$O, sodium carbonate-$^{18}$O, sodium nitrate-$^{18}$O, sodium nitrite-$^{18}$O, sodium perchlorate-$^{18}$O, sodium sulfate-$^{18}$O, sulfur dioxide-$^{18}$O, sulfuric acid-$^{18}$O, urea-$^{18}$O, and valine-$^{18}$O.

In one embodiment, the ratio of the shortest dimension of the capsule to the longest dimension of the capsule is in the range of 1:30 to 1:1, preferably 1:27 to 1:1, more preferably 1:25 to 1:1. In one embodiment the capsule has a shortest dimension of 0.01 to 4 mm, preferably 0.4 to 3 mm, more preferably 0.8 to 2 mm. In one embodiment the capsule has a longest dimension of 0.02 to 50 mm, preferably 1 to 35 mm, more preferably 2 to 20 mm.

The capsule may have a cuboid, spheroid, ovoid, ellipsoid, or other irregular shape, and with ends that may be rounded, squared, tapered, beveled, conical, concave, convex, scalloped, angular, or in some other form.

In one embodiment, the capsule is of a size that can be easily implanted into or next to a tumor in an organism by a needle and syringe, a catheter, or a brachytherapy seed applicator. In another embodiment, the capsule may dissolve or disintegrate within the organism after a certain period of time following the imaging procedure.

In one embodiment, the polymer layer may be thick enough to contain particles such as nanoparticles or microparticles. The polymer layer may have a thickness of 20 nm-200 µm, preferably 1 µm-100 µm, more preferably 4 µm-50 µm. It can be envisioned that the capsule is composed of more than one separated polymer layer. The separated layers could be in a concentric multilamellar arrangement, or in the case of three or more polymer layers, two or more interior polymer layers could encapsulate separate volumes. In an alternative arrangement, the polymer layers may be interconnected while encapsulating separate volumes. The weight of the polymer layer, or all polymer layers, may make up 0.1-70%, preferably 1-60%, more preferably 5-50% of the total capsule weight.

In another embodiment the external surface of the biocompatible polymer layer is corrugated or knurled to limit movement within an organism. As used herein, "corrugated or knurled" refers to the external surface having a plurality of raised and depressed portions. The peaks of the raised portions may be spaced by an average of 0.1-100 µm, preferably 10-80 µm, more preferably 20-60 µm. The external surface of the polymer layer may also be textured at smaller scales to limit movement, and the roughness of these textures can be characterized by atomic force microscopy (AFM). For example, a 100 nm×100 nm region of the external surface measured by AFM may possess an RMS roughness of at least 1 nm, preferably at least 10 nm, more preferably at least 20 nm.

In one embodiment, the biocompatible polymer is selected from, but not limited to, a fluoropolymer, a polyarylether ketone, a polyether, a polyester, a polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, a polysiloxane, a polyvinylfluoride (PVF), a polyvinylidene fluoride (PVDF), a polytetrafluoroethylene (PTFE), a polychlorotrifluoroethylene (PCTFE), a perfluoroalkoxy (PFA) polymer, a fluorinated ethylene-propylene (FEP) copolymer, a polyethylenetetrafluoroethylene, a polyethylene chlorotrifluoroethylene (ECTFE), a poly(chlorotrifluoroethylene-co-vinylidene fluoride), a perfluoropolyether (PFPE), a perfluorosulfonic acid, an acrylonitrile butadiene styrene (ABS) copolymer, a styrene-butadiene copolymer, a styrene-acrylonitrile copolymer, an ethylene-vinyl acetate (EVA) copolymer, an ethylene vinyl alcohol copolymer, a polyethylene terephthalate (PET), a polycyclohexylene dimethylene terephthalate (PCT), a polyhydroxyalkanoate, a polyethylene (PE), a polyetheretherketone (PEEK), a polyetherketoneketone (PEKK), a polyetherimide (PEI), a polyethersulfone (PES), a polylactic acid (PLA), a polyglycolic (PGA), a poly(lactic-co-glycolic acid) (PLGA), a polymethylpentene (PMP), a polyphenylene oxide (PPO), a polyphenylene sulfide (PPS), a polypropylene (PP), a polystyrene (PS), a polytrimethylene terephthalate (PTT), a polyvinyl acetate (PVA), a polyvinyl chloride (PVC), a polyvinylidene chloride (PVDC), a polydicyclopentadiene (PDCPD), a polyacrylonitrile (PAN), cellulose acetate phthalate (CAP), hydroxypropyl methylcellulose phthalate (HPMCP), polyvinyl acetate phthalate (PVAP), hydroxypropylmethyl cellulose, hydroxypropyl methylcellulose acetate succinate (HPMCAS), cellulose acetate trimellitate, hydroxypropyl methylcellulose succinate, carboxymethyl cellulose, carboxymethyl ethyl cellulose, cellulose acetate phthalate, cellulose acetate succinate, cellulose acetate hexahydrophthalate, cellulose propionate phthalate, cellulose acetate maleate, cellulose acetate butyrate, cellulose acetate propionate, a copolymer of methylmethacrylic acid and methyl methacrylate, a copolymer of methyl acrylate, methylmethacrylate and methacrylic acid, a copolymer of methylvinyl ether and maleic anhydride, polyvinyl acetate phthalate, zein, shellac, Eduragit L 30 D-55, Eudragit FS 30 D, Eudragit L 100, Eudragit S 100, Kollicoat EMM 30D, Estacryl 30D, or any mixture thereof.

Preferably, the polymer layer comprises a fluoropolymer, a polyarylether ketone, a polyether, a polyester, a polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, or a polysiloxane. Preferably, the polymer layer consists essentially of a polyester.

In one embodiment, the contrast agent may be active under either MRI or X-ray imaging. Alternatively, the contrast agent may be active under only one mode of imaging.

In another embodiment, the contrast agent is a metallic particle with a largest dimension less than 10 µm, preferably less than 5 µm, more preferably less than 1 µm.

The contrast agent may be a metal with an atomic number greater than 20. In one embodiment, the contrast agent is a metallic particle or metallic compound containing a metal such as, but not limited to, barium, bismuth, cobalt, copper, gadolinium, gold, hafnium, iridium, iron, manganese, nickel, palladium, platinum, rhenium, silver, tantalum, thallium, titanium, tin, tungsten, and vanadium.

In one embodiment the contrast agent is a metal oxide. The metal oxide may comprise a metal with an atomic number greater than 20. Suitable metal oxides include, but are not limited to, barium oxide, bismuth oxide, cobalt oxide, copper oxide, gadolinium oxide, hafnium oxide, iridium oxide, iron oxide, manganese oxide, nickel oxide, palladium oxide, silver oxide, tantalum oxide, thallium oxide, titanium oxide, tin oxide, tungsten oxide, or vanadium oxide. In a preferred embodiment, the metal oxide is gadolinium oxide. To function as a source of positrons, the metal oxide may be enriched in $^{18}O$ to at least 30 mol %, preferably to at least 50 mol %, more preferably to at least 80 mol % of the total oxygen.

In one embodiment the capsule may contain metallic compounds or particles comprising a ferromagnetic metal, including, but not limited to nickel, iron, cobalt, gadolinium, or manganese. Additionally, commercial gadolinium-based contrast agents can be used, including, but not limited to, gadopentetate dimeglumine (Magnevist), gadobenate dimeglumine (MultiHance), gadobutrol (Gadovist/Gadavist), gadoterate meglumine (Dotarem), gadodiamide (Omniscan), gadoversetamide (OptiMARK), gadoxetate disodium (Primovist/Eovist), and gadoteridol (ProHance).

In one embodiment the contrast agent may be functionalized with ligands to reduce its toxicity to the organism, improve solubility within the capsule, and in some cases, increase the relaxivity of an MRI contrast agent. These ligands may be ethylenediaminetetraacetic acid (EDTA), diethylenetriaminepentaacetic acid (DTPA), diethylenetriamine pentaacetic acid bismethoxyethylamide (DTPA-BME), citric acid, or dexrazoxane.

In one embodiment the capsule may contain a non-metallic contrast agent, such as an iodine compound. Examples of non-metallic iodinated X-ray contrast agents include, but are not limited to, diatrizoic acid, sodium metrizoate, sodium ioxaglate, iopamidol, and iohexol.

In one embodiment the capsule comprises more than one type of contrast agent. For example, the $^{18}$O-water can contain an X-ray imaging contrast agent such as barium sulfate, and a magnetic resonance imaging contrast agent, such as gadopentetate dimeglumine. The ferromagnetic compound may be present at a molar ratio to the X-ray imaging contrast agent in a range of 1:100 to 100:1, preferably 1:50 to 50:1, preferably 1:10 to 10:1, and more preferably 1:1.2 to 1.2:1. For a capsule containing one or more contrast agents, the total weight of the contrast agent or agents may be 0.01-70%, preferably 0.1-60%, more preferably 1-50% of the total weight of the capsule. FIG. 1 is an example embodiment of a capsule containing two contrast agents. A biocompatible polymer layer 12 encloses a volume of $^{18}$O-enriched water 10 containing a metallic X-ray imaging contrast agent 14 and a ferromagnetic compound 16.

Figure 2A:
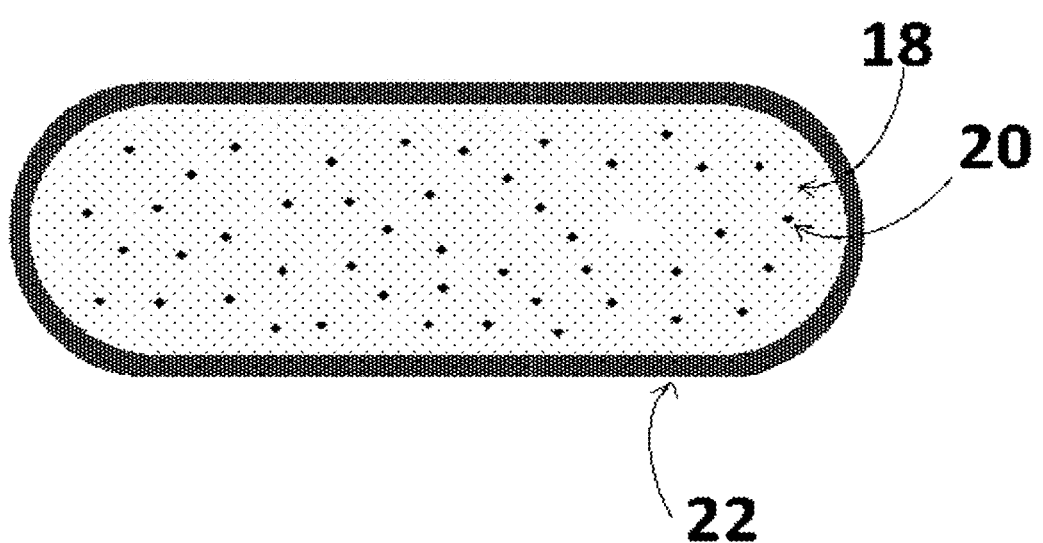
FIG. 2A is an embodiment of a positron emitter capsule with the X-ray imaging contrast agent distributed evenly within the polymer layer.
Figure 2B:
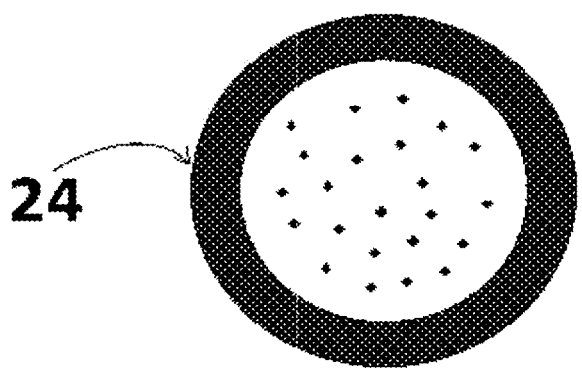
FIG. 2B shows a cross-section view.

In one embodiment the contrast agent is located on an external surface of the polymer layer, dispersed within the polymer layer, dispersed within the volume of $^{18}$O-enriched water, or any combination thereof. When the contrast agent is located on the surface of the polymer layer, the exposed surface area of the contrast agent may be 0.01-70%, preferably 1-60%, more preferably 5-50% of the entire external surface area of the capsule. A contrast agent dispersed within the layer may result from mixing the contrast agent with the biocompatible polymer during its formation process. A contrast agent may be dispersed in the polymer layer to take up a volume percentage of the total polymer layer volume of 0.01-60%, preferably 0.1-40%, more preferably 1-20%. As an example, FIG. 2A is a capsule with a polymer layer 22 enclosing a ferromagnetic compound 20 in $^{18}$O-enriched water 18. FIG. 2B is a cross-section view of the capsule, which shows the even distribution of the X-ray imaging contrast agent 24 within the polymer layer. In general, a contrast agent dispersed within the polymer layer may also be exposed on the exterior surface of the capsule, and the rate of this occurrence would depend on the thickness of the polymer layer, the concentration of the contrast agent, and the size of the contrast agent.

Figure 3:
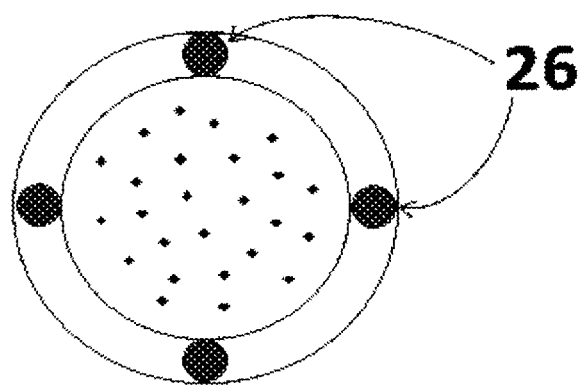
FIG. 3 is a cross-section view of a positron emitter capsule embodiment with the X-ray imaging contrast agent distributed heterogeneously throughout the polymer layer, in the form of agglomerates.
Figure 4A:
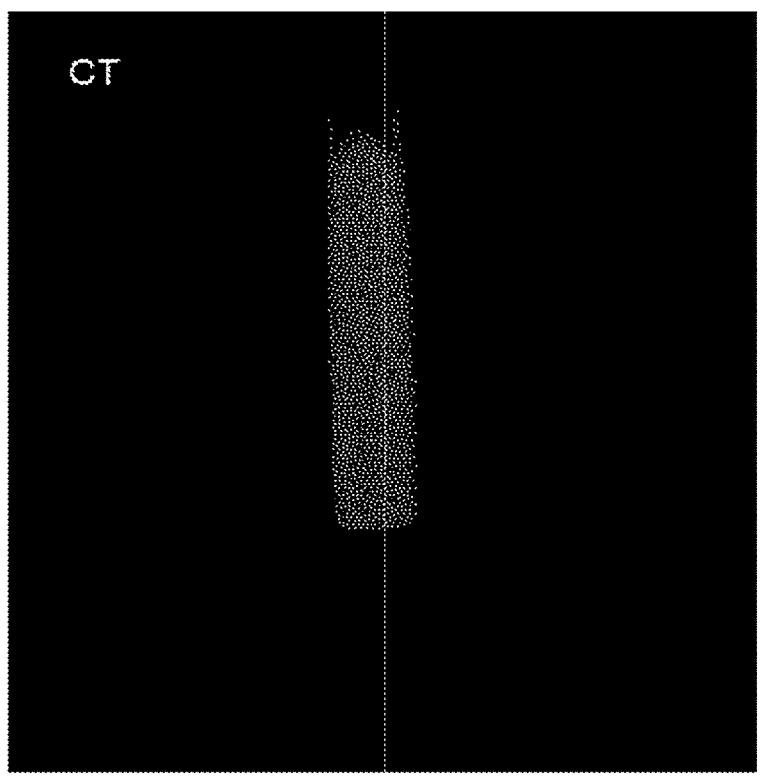
FIG. 4A is a CT image side view of $^{18}$O-enriched water suspended in gelatin after clinical proton beam irradiation.
Figure 4B:
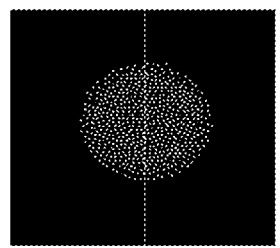
FIG. 4B is a top view.
Figure 5A:
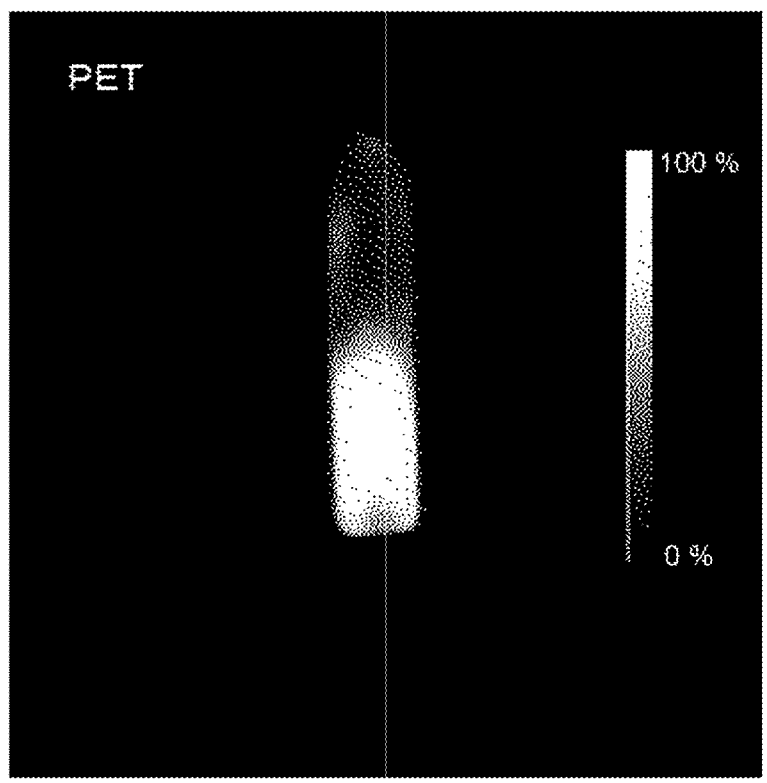
FIG. 5A is a PET image side view of the same $^{18}$O-enriched water suspended in gelatin after clinical proton beam irradiation, showing a profile of the spread-out Bragg peak (SOBP).
Figure 5B:
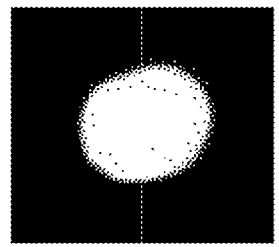
FIG. 5B is a top view.
Figure 6A:
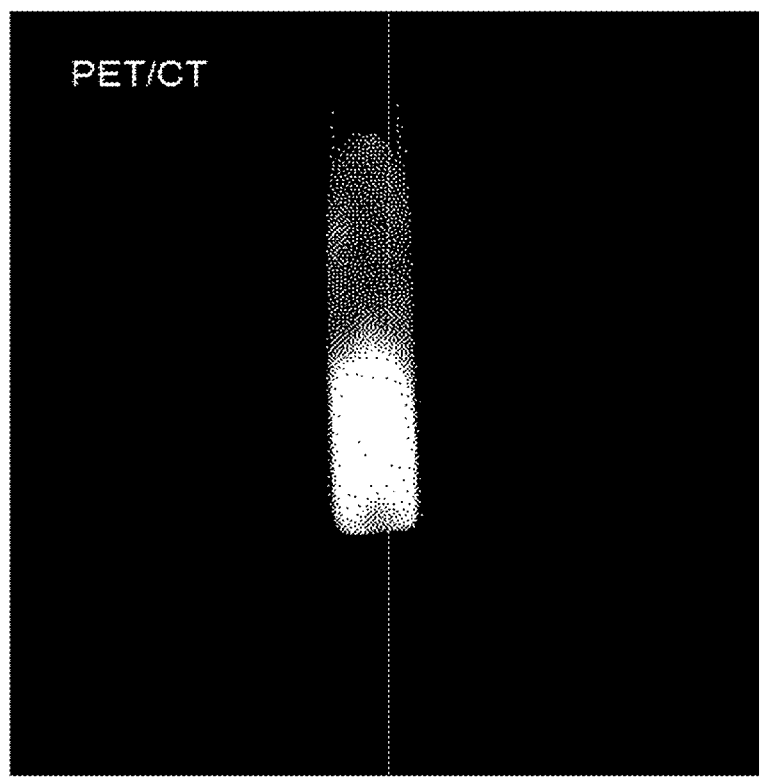
FIG. 6A is an image overlay of the PET/CT images from FIG. 4A and FIG. 5A.
Figure 6B:
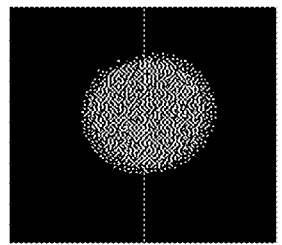
FIG. 6B is the corresponding top view of the image overlay.
Figure 7A:
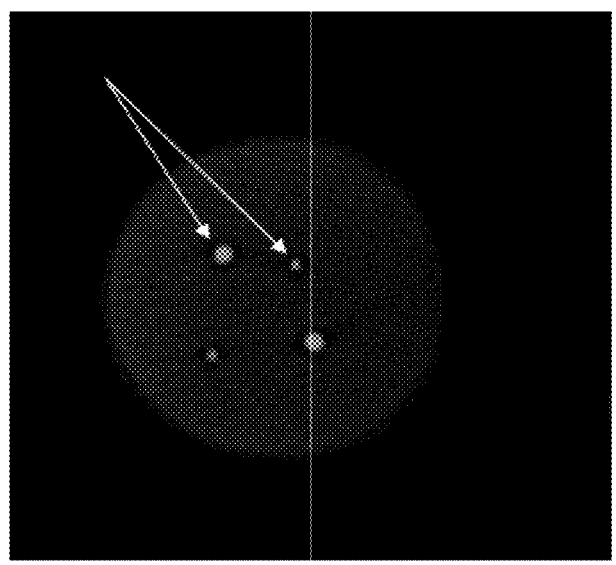
FIG. 7A is a CT image of capsules encapsulating a radiopaque suspension of 3 mM bismuth oxide nanoparticles in $^{18}$O-enriched water.
Figure 7B:
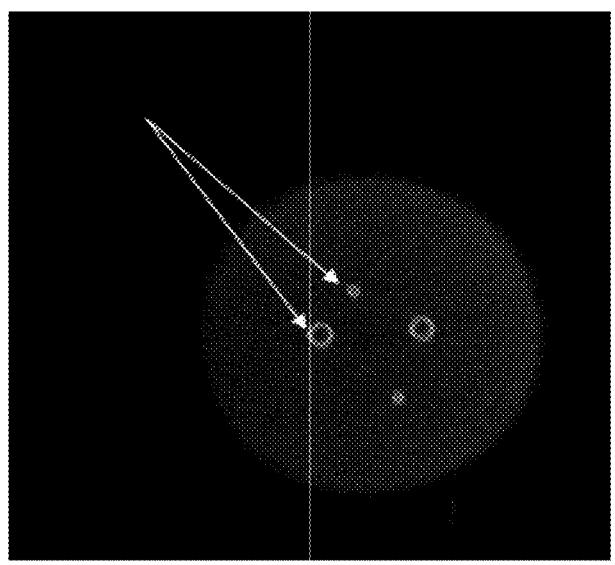
FIG. 7B is a CT image of capsules containing an 8% barium compound mixed into the polymer layer starting material before the polymerization process.
Figure 8A:
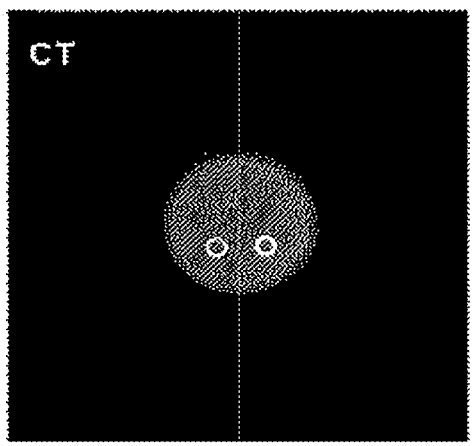
FIG. 8A is a micro CT image top view of different sizes of the positron emitter capsule after irradiation with a 160 MeV clinical proton beam.
Figure 8B:
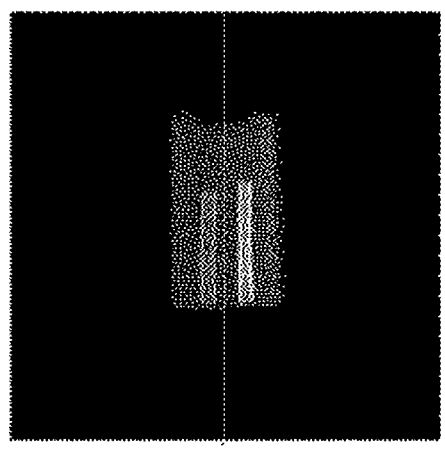
FIG. 8B is a side view.
Figure 9A:
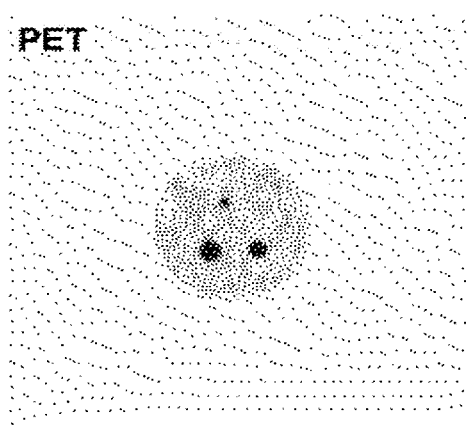
FIG. 9A is a PET image top view of FIG. 8A, with FIG. 9B being the corresponding side view, with the proton-activated capsules clearly visible in both CT and PET images.
Figure 9B:
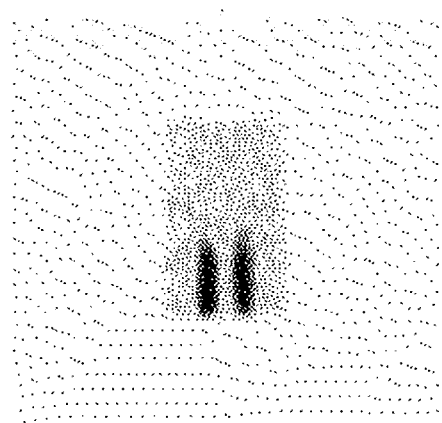
Figure 10A:
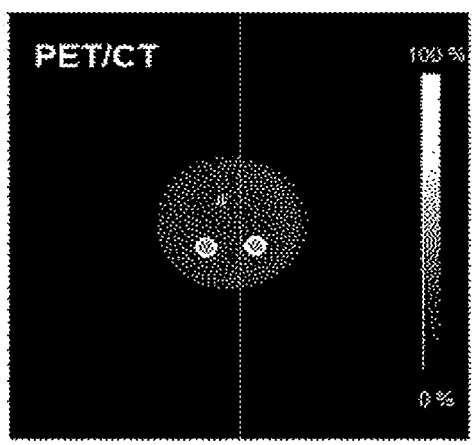
FIG. 10A is an image overlay of FIG. 8A and FIG. 9A.
Figure 10B:
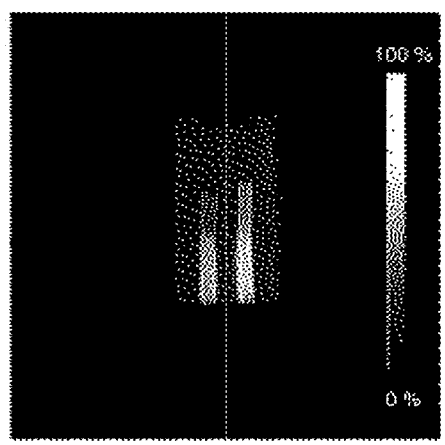
FIG. 10B is an image overlay of FIG. 8B and FIG. 9B.

In one embodiment the contrast agent is present in the form of agglomerates. As used herein, the term "agglomerates" refers to a clustered particulate composition comprising primary particles, the primary particles being aggregated together in such a way so as to form clusters thereof, at least 50 volume percent of the clusters having a mean diameter that is at least 2 times the mean diameter of the primary particles, and preferably at least 90 volume percent of the clusters having a mean diameter that is at least 5 times the mean diameter of the primary particles. The primary particles may be comprised of one or more compounds and may include nanoparticles and microparticles. These agglomerates may have a largest dimension between 10 nm and 200 µm, preferably 30 nm and 50 µm, more preferably 50 nm and 2 µm, and are located on an external surface of the polymer layer or within the polymer layer. Agglomerates mixed into the polymer layer during the capsule formation process may lead to some agglomerates exposed on the external surface of the polymer layer, with some located entirely within the polymer layer. FIG. 3 shows a cross-section view of agglomerates 26 dispersed in the biocompatible polymer layer.

In one embodiment the capsule includes a stable isotope, present as part of a molecule or compound, capable of being proton-activated into a positron-emitting isotope. The term "stable isotope" refers to an isotope that will not spontaneously undergo a radioactive process on its own, including radioactive decay. With regards to the current invention, the proton-activation occurs when the isotope is irradiated with the proton beam, inducing a photonuclear reaction by which the isotope gains a proton and becomes an unstable isotope. Following this proton-activation, the unstable isotope decays, possibly by a decay mode that emits positrons. For example, $^{63}$Cu is a stable isotope that can be proton-activated into $^{63}$Zn upon irradiation with a proton beam. $^{63}$Zn is an unstable isotope with a half-life of 38 minutes and will decay back into $^{63}$Cu by an electron capture or positron emission decay mode.

The proton-activatable isotope, present as part of a molecule or compound, may be dispersed in the $^{18}$O-enriched water, dispersed within the polymer layer, located on the external surface of the polymer layer, or any combination thereof. Upon activation by a proton beam, this isotope emits positrons, further enhancing the PET signal. This proton-activatable isotope includes but is not limited to $^{89}$Y, $^{63}$Cu, $^{65}$Cu, $^{64}$Zn, $^{66}$Zn, $^{67}$Zn, $^{68}$Zn, $^{70}$Zn, $^{69}$Ga, $^{71}$Ga, $^{30}$Si, $^{15}$N, $^{13}$C, or $^{11}$B. The preferred concentration of each isotope in the capsule is dependent on the proton-induced yield of each isotope. In a single capsule, the total weight of the proton-activatable isotope or isotopes may make up 0.01-70% of the total weight of the capsule, preferably 0.05-55%, more preferably 0.1-40%. The isotopes may be complexed with a ligand suitable for PET imaging, such as diacetyl-bis(N(4)-methylthiosemicarbazone) (ASTM), pyruvaldehyde-bis(N4-methylthiosemicarbazone) (PTSM), DOTATOC (edotreotide), DOTA-TATE, and DOTA-NOC. Or, the isotopes may be present in smaller molecules such as [$^{30}$Si]-sodium silicate, $^{15}$NH$_3$, $^{13}$CH$_3$OH, [$^{13}$C]-acetate, and [$^{11}$B]-boric acid.

In one embodiment, the capsule further encapsulates a porous, water permeable polymeric matrix. This polymeric matrix is used to restrict the movement of a contrast agent dispersed in the $^{18}$O-enriched water. The polymeric matrix may compose 0.01-50%, preferably 0.1-40%, more preferably 1-30% of the total weight of the capsule. This polymeric matrix may comprise any of the aforementioned polymers that could be used in the biocompatible polymer layer, or a mixture thereof. The polymeric matrix of a capsule may be made from the same polymer as used in the polymer layer, but preferably, the polymers are different. The polymeric matrix may also be made of polymers such as polyethylene glycol, sodium alginate, carrageenan, gelatin, polyvinylpyrrolidone, crospovidone, croscarmellose sodium, or sodium starch glycolate.

According to a second aspect, the present disclosure relates to a method of treating a tumor in an organism with a proton beam. First, the capsule is administered to the organism in order to place the capsule next to or inside the tumor. Modes of administration may include, but are not limited to, oral administration, topical administration, rectal administration, urethral administration, intravaginal administration, intradermal injection, subcutaneous injection, intramuscular injection, intralesional injection, intratumoral injection, epidural injection, intracranial injection, and sublingual administration. Preferably, the mode of administration is by intratumoral injection or oral administration.

It can be envisioned that the capsule would be administered with a pharmaceutically acceptable carrier or lubricant in order to assist in injection or implantation. Such carrier or lubricant may include, but is not limited to, a hydrogel or a buffered solution of mannitol, xylitol, sorbitol, maltitol, magnesium stearate, saline, or sodium dodecyl sulfate. The ratio of the total volume of the injected carrier or lubricant to the total volume of the capsule may range from 100:1 to 1:10, preferably 50:1 to 1:5, more preferably 10:1 to 1:1. In the case of topical administration, it is envisioned that the capsule may be secured to an exterior surface of the organism by an adhesive before imaging. For modes of administration involving injection, it is envisioned that a pharmaceutically active molecule may be injected simultaneously with the capsule. This pharmaceutically active molecule may be a local anesthetic or an antineoplastic agent, and may make up 0.001-10, preferably 0.01-7, more preferably 0.1-5% of the total weight of the carrier or lubricant.

The organism may be *Homo sapiens sapiens, Pan troglodytes, Bos primigenius, Sus scrofa domesticus, Canis lupus familiaris, Felis catus, Rattus norvegicus, Mus musculus,* or *Equus ferus caballus*. Preferably, the organism may be *Homo sapiens sapiens*.

The tumor may include, but is not limited to, tumors of the cervix, prostate, breast, skin, lung, brain, eye, mouth, GI tract, urinary tract, liver, pancreas, testes, thyroid, base of skull, or kidney. It is further envisioned that the capsule could be used with other types of diseased tissues that would benefit from proton beam therapy.

In one embodiment, two or more capsules are administered. These capsules could be administered by the same mode of administration or injection, or by different modes. The placing of more than one capsule could allow for the capsules to be located on opposite sides of the tumor, or, the capsules may be located next to each other, or more than one capsule could be placed inside the tumor, or at least one capsule could be placed outside the tumor, with at least one placed inside the tumor.

Second, the capsule is located with computed tomography (CT), magnetic resonance imaging (MRI), ultrasonography, or X-ray imaging, from a signal produced by the capsule. This information is used to align and configure the proton beam to a certain entry point and depth to irradiate the capsule and/or tumor in the organism. In the case of an imaging device that combines one of the aforementioned imaging modes with proton beam therapy, the alignment of the proton beam may occur automatically. In the case of separate devices, it is envisioned that the exterior of the organism would need to be marked in order to show the location of the capsule and/or tumor. If the organism is moved to a different location for the proton beam therapy, the marking would stay in place. This marking could be by temporary means on the organism's exterior surface, such as a dye, ink, or an adhesive label. Or, it may be by mechanical means, such as a brace encompassing the entire organism or a part of the organism, and which shows where to align the beam.

Figure 11:
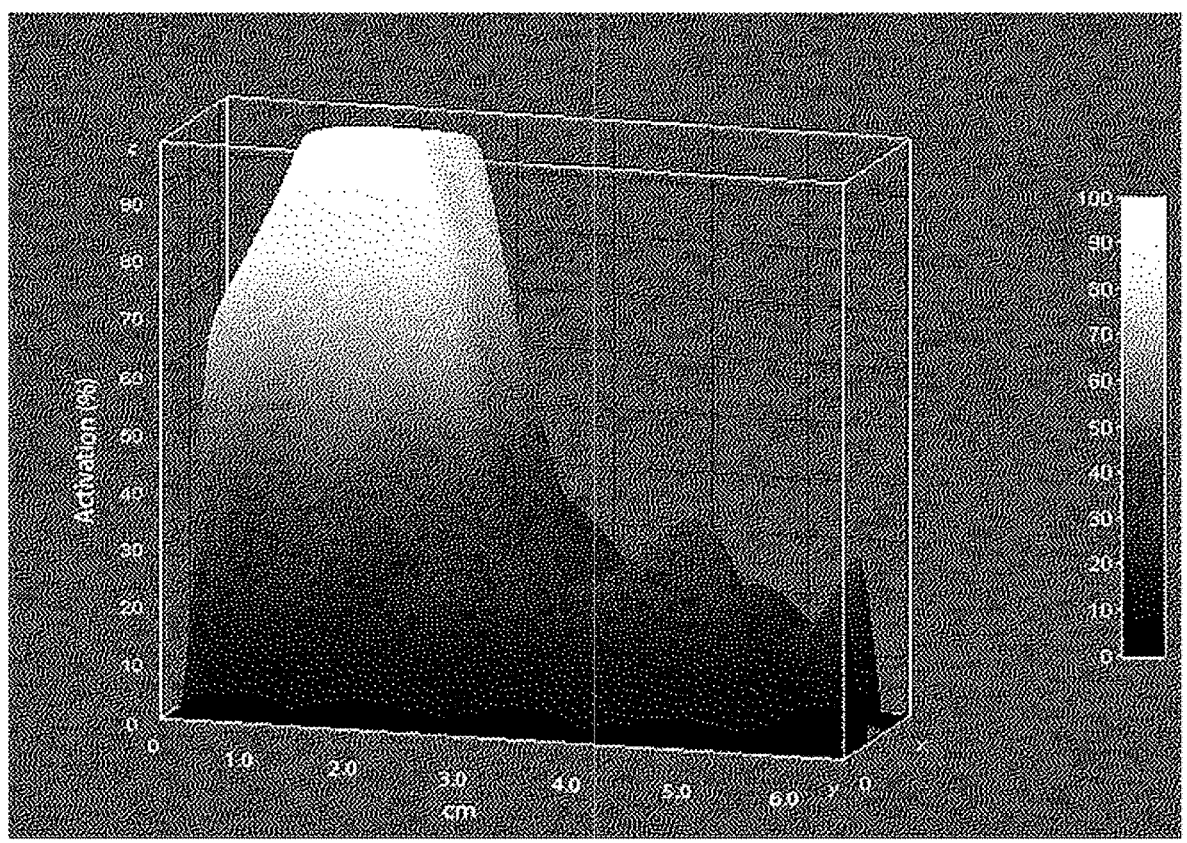
FIG. 11 is a measurement of the clinical proton beam profile used in the positron emitter capsule testing.
Figure 12:
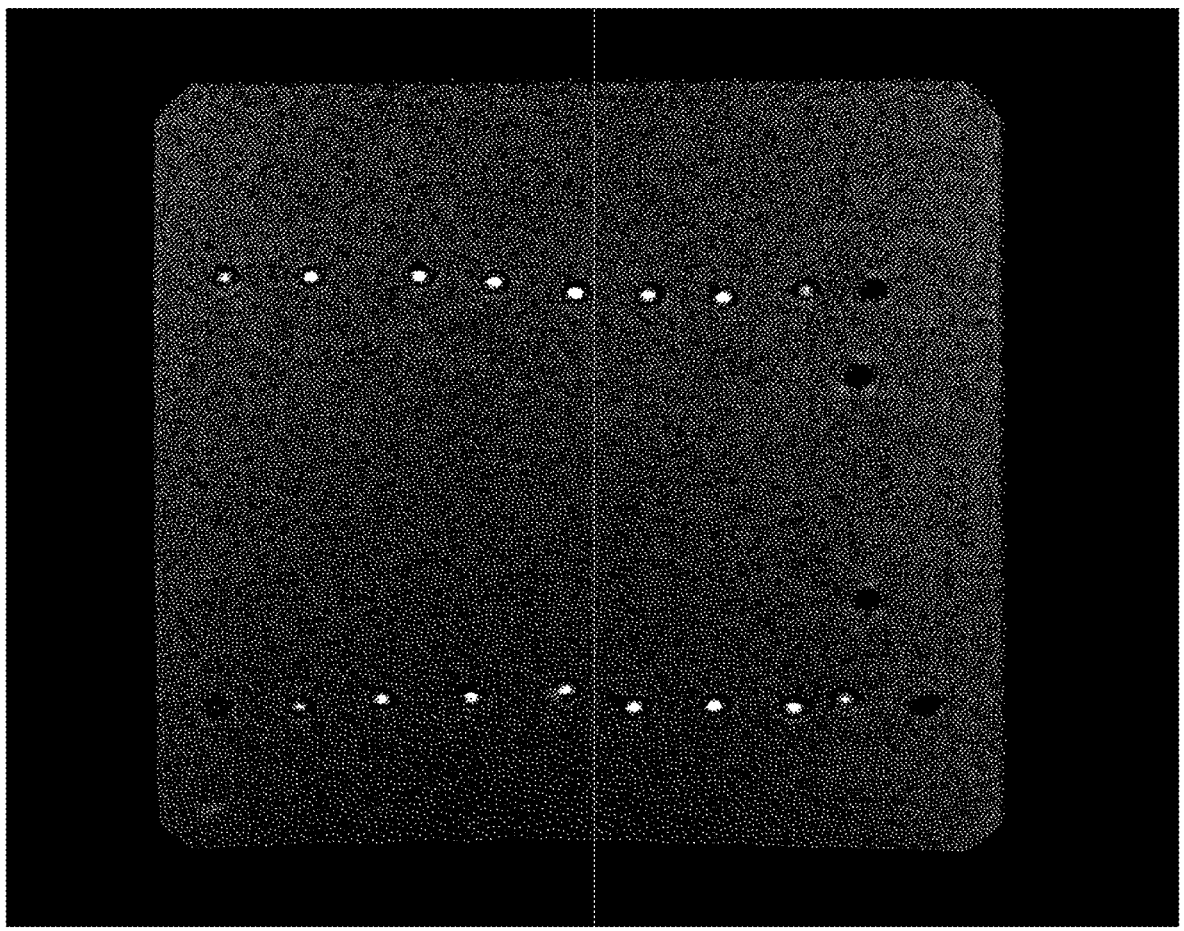
FIG. 12 is an MRI T1 image of capsules containing both $^{18}$O-enriched water and different concentrations of gadolinium oxide nanoparticles.

Third, having positioned the organism and aligned the proton beam to the needed entry angle and depth, the tumor and capsule are irradiated with a clinical 1-500 MeV, preferably 10-400 MeV, more preferably 50-300 MeV power proton beam from outside the organism. The proton beam may comprise protons with a distribution of energies, in order to create and modulate the spread-out Bragg peak (FIG. 11). The source of the proton beam may be a particle accelerator such as a cyclotron, synchrotron, or a linear accelerator; preferably the source is a cyclotron. The proton beam may exit a nozzle right before entering the organism, and this nozzle may be on a rotating gantry or in a fixed position. In order to irradiate the target completely, the proton beam path at a single alignment angle may be finely manipulated through scattering or scanning the beam, and changing the power. Scanning the beam may involve steering and deflecting the beam with magnets. Scattering may involve passing the beam through apertures and collimators to expand the proton beam to irradiate a larger area. Changing the power may change the depth of the proton beam in the organism or the shape of the spread-out Bragg peak.

In the embodiment where more than one capsule is administered, depending on their relative positions, the capsules may be irradiated together by a single alignment of the proton beam, or the proton beam may be adjusted to irradiate one capsule, and then another. It is further envisioned that a single tumor and capsule may be irradiated more than once, at different angles.

Proton beam therapy of a tumor involves delivering an appropriate dose of radiation to a tumor, whereby the tumor's DNA is damaged by the ionizing effect of the proton beam. With this damage, the tumor cells are unable to replicate. The appropriate dose depends on several variables relating to the proton beam and the tumor, including, but not limited to, proton beam power, width, length of exposure, and rate of scanning; tumor depth, size, type, and proximity to sensitive tissues or organs. A radiologist having ordinary skill in the art can readily determine and deliver an effective dose of proton beam irradiation. In the case of the present invention, which uses a capsule to assist in initial beam alignment and subsequent PET imaging, capsule size, location, isotope type, and isotope concentration may also be considered by the radiologist in determining the appropriate dose.

Upon irradiation by the proton beam, $H_2{}^{18}O$ molecules undergo a $^{18}O(p,n)^{18}F$ photonuclear reaction and are converted to an aqueous radioisotope $^{18}F^-$ fluoride ion within the capsule. In one embodiment, it is envisioned that other molecules containing $^{18}O$, as previously listed, could also produce $^{18}F^-$ fluoride ion upon irradiation. In the embodiment where other proton-activatable isotopes are present, it is envisioned that those isotopes undergo photonuclear reactions and also emit positrons upon radioactive decay.

Following the $^{18}O(p,n)^{18}F$ photonuclear reaction, the radioisotope $^{18}F^-$ fluoride ion has a long half-life (110 minutes), and decays by either positron emission (~97% of decays), or electron capture (~3% of decays). The positron emission of each $^{18}F^-$ fluoride ion results in two 511 keV gamma rays (positrons), emitted at a relative angle of 180°. Positrons captured by PET detectors produce a first set of image and location data of the tumor and tumor environment. Both positron emission and electron capture decay modes yield stable $^{18}O$, which can be irradiated again by the proton beam to produce the $^{18}F^-$ fluoride ion.

In the embodiment where the capsule contains other proton-activatable isotopes along with or in place of the $^{18}O$-enriched water, it is envisioned that the proton beam irradiation also causes those isotopes to emit detectable positrons, although the radiation efficiency and decay rates may be different.

In another embodiment, the PET detector is located off-site in relation to the proton beam, meaning, at a separate facility. Due to the long half-life of the $^{18}F^-$ fluoride ion, it is envisioned that the organism could receive the proton beam irradiation at one facility and have the time to be transported to a different facility for the PET imaging. Or, the PET detector may be located on-site within the same facility, but in a separate device. Or, the PET detector may be located within the same device as the proton beam. It is further envisioned that the first step of locating the capsule (by MRI, X-ray, or ultrasonography) could be performed by a single machine that also comprises the proton beam and the PET detector, allowing all imaging steps to be performed without having to move the organism.

Within the lifetime of the $^{18}F^-$ fluoride ion, several rounds of PET image and location data may be recorded of the tumor and capsule. Depending on the concentration and total amount of $^{18}F^-$ fluoride ion present in the capsule, as well as the sensitivity of the PET detector, images may be recorded as long as 8 hours after the proton beam irradiation. Preferably, the images may be recorded within 2 hours after the proton beam irradiation.

In a further embodiment, the tumor and capsule are irradiated again with the proton beam to produce a second set of image and location data. It is conceivable that this second irradiation may occur long after the first irradiation, such as over 8 hours, at which time the positron emission signal from $^{18}F^-$ fluoride ion decay would be weak. Or, the second irradiation may follow much earlier, possibly within 1 minute, if a small dose of proton beam irradiation was delivered the first time.

In one embodiment, this second set of image and location data is compared to the first set in order to track the movement of the tumor. Or, image and location data may be compared within a particular set. With knowledge of the tumor movement, the proton beam alignment or the position of the organism can be readjusted to allow effective proton beam therapy. It is conceivable that an incorporated PET imaging and proton beam therapy system could make frequent adjustments automatically to account for small movements of the tumor. Such movements may result from the organism's breathing or muscle twitching. Tracking a tumor over longer periods of time may be used to observe the growth or shrinkage of the tumor in order to make adjustments to the proton beam therapy or other types of therapy.

In another embodiment, this second set of image and location data is compared to the first set in order to track the movement of the capsule. Or, image and location data may be compared within a particular set. In the case that the capsule moves too far from the tumor to provide clear PET imaging, the proton beam therapy may be suspended until the capsule is repositioned. Or, in the case of a capsule administered orally, the position of the capsule may be monitored to track its progression through the GI tract towards or away from a certain tumor site.

The optimal length of time between PET image and location data for tracking the tumor or capsule depends on the speed of the PET detector, the area imaged, and the purpose of tracking. To track the movement of a tumor and capsule caused by breathing would require images taken faster than the organism's respiration rate. In that case, the time period between images would likely be under 1 second. At the other side of the timescale, tracking the growth or shrinkage of a tumor may rely on images taken at time intervals of hours or days.

Depending on the mode of administration and the composition of the capsule, it is conceivable that the capsule would need to be manually removed from the organism at the conclusion of irradiation and imaging. For an embodiment requiring manual removal, it is further envisioned that an implanted capsule could be attached to a tether for ease of extraction. For some modes of administration, such as oral administration, the capsule would exit the organism on its own through the GI tract. For an envisioned embodiment of the capsule made completely of biocompatible materials with a biodegradable or dissolvable exterior surface, the capsule would not need to be manually removed. In that envisioned embodiment, the capsule would dissolve following the decay of most of the $^{18}F^-$ to $^{18}O$, in order to reduce risk to the organism.

The foregoing paragraphs have been provided by way of general introduction, and are not intended to limit the scope of the following claims.

The invention claimed is:

1. A positron emitter capsule comprising:
   a biocompatible encapsulating polymer layer;
   a volume of $^{18}O$-enriched water, wherein the $^{18}O$-enriched water is encapsulated by the biocompatible encapsulating polymer layer; and
   a contrast agent which is active under magnetic resonance imaging (MRI) or X-ray imaging.

2. The positron emitter capsule of claim 1 which has a shortest dimension of 0.8 to 2 mm and a longest dimension of 2 to 20 mm.

3. The positron emitter capsule of claim 1 wherein the contrast agent is a metallic particle with a largest dimension less than 1 μm.

4. The positron emitter capsule of claim 1 wherein the contrast agent is at least one metallic particle or metallic compound selected from the group consisting of barium, bismuth, cobalt, copper, gadolinium, gold, hafnium, iridium, iron, manganese, nickel, palladium, platinum, rhenium, silver, tantalum, thallium, titanium, tin, tungsten, and vanadium.

5. The positron emitter capsule of claim 1 wherein the contrast agent is a metal oxide.

6. The positron emitter capsule of claim 5 wherein the metal oxide is barium oxide, bismuth oxide, cobalt oxide, copper oxide, gadolinium oxide, hafnium oxide, iridium oxide, iron oxide, manganese oxide, nickel oxide, palladium oxide, silver oxide, tantalum oxide, thallium oxide, titanium oxide, tin oxide, tungsten oxide, or vanadium oxide.

7. The positron emitter capsule of claim 1 wherein the contrast agent is located on an external surface of the biocompatible encapsulating polymer layer and/or dispersed within the biocompatible encapsulating polymer layer which covers the $^{18}O$-enriched water.

8. The positron emitter capsule of claim 1 wherein the contrast agent is present in the form of agglomerates having a largest dimension between 50 nm and 2 μm, and the agglomerates are dispersed on an external surface of the biocompatible encapsulating polymer layer or dispersed within the biocompatible encapsulating polymer layer.

9. The positron emitter capsule of claim 1 wherein an external surface of the biocompatible encapsulating polymer layer is corrugated or knurled to limit movement within an organism,
   wherein the external surface has a plurality of raised portions having an average spacing in a range of 0.1-100 μm.

10. The positron emitter capsule of claim 1 wherein the biocompatible encapsulating polymer layer comprises at least one polymer selected from the group consisting of a fluoropolymer, a polyarylether ketone, a polyether, a polyester, a polyamide, a polyimide, a polyurethane, a polycarbonate, a polyanhydride, a polyurea, a polyolefin, a polystyrene, a polysulfone, a polysulfide, a polyketone, a poly(methyl acrylate), a polymethacrylamide, a vinyl polymer, and a polysiloxane.

11. The positron emitter capsule of claim 1 further comprising a second stable isotope, present as part of a molecule or compound, wherein the second stable isotope is capable of being proton-activated into a positron-emitting isotope.

12. The positron emitter capsule of claim 11 wherein the second stable isotope is selected from the group consisting of $^{89}$Y, $^{63}$Cu, $^{65}$Cu, $^{64}$Zn, $^{66}$Zn, $^{67}$Zn, $^{68}$Zn, $^{70}$Zn, $^{69}$Ga, $^{71}$Ga, $^{30}$Si, $^{15}$N, $^{13}$C and $^{11}$B.

13. A method of treating a tumor in an organism, comprising:
    administering the positron emitter capsule of claim 1 to the organism;
    locating the positron emitter capsule with computed tomography (CT), magnetic resonance imaging (MRI), ultrasonography, or X-ray imaging, from a signal produced by the positron emitter capsule;
    irradiating the tumor and positron emitter capsule with a proton beam from outside the organism to convert the $^{18}$O-enriched water to an aqueous radioisotope $^{18}$F$^-$ fluoride ion within the positron emitter capsule by a photonuclear reaction, whereby the radioisotope $^{18}$F$^-$ fluoride ion emits positrons; and
    imaging the tumor and tumor environment by measuring the emitted positrons with a positron emission tomography (PET) detector to produce a first set of image and location data.

14. The method of claim 13, wherein the positron emitter capsule is administered by injecting the positron emitter capsule into the organism, next to or inside the tumor.

15. The method of claim 13, wherein the positron emitter capsule is administered orally.

16. The method of claim 13, wherein the positron emission tomography detector is located off-site in relation to the proton beam.

17. The method of claim 13, further comprising repeating the irradiating to produce a second set of emitted positrons.

18. The method of claim 17, further comprising imaging the second set of emitted positrons to produce a second set of image and location data.

19. The method of claim 18, further comprising tracking the movement of the tumor by comparing the first and second set of image and location data.

20. The method of claim 18, further comprising tracking the movement of the positron emitter capsule by comparing the first and second set of image and location data.

* * * * *